US008029556B2

(12) United States Patent
Rowe

(10) Patent No.: US 8,029,556 B2
(45) Date of Patent: Oct. 4, 2011

(54) METHOD AND APPARATUS FOR RESHAPING A VENTRICLE

(75) Inventor: Stanton J. Rowe, Newport Beach, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 680 days.

(21) Appl. No.: 11/695,583

(22) Filed: Apr. 2, 2007

(65) Prior Publication Data

US 2008/0086164 A1 Apr. 10, 2008

Related U.S. Application Data

(60) Provisional application No. 60/849,242, filed on Oct. 4, 2006.

(51) Int. Cl.
*A61F 2/06* (2006.01)
(52) U.S. Cl. .................. 623/1.21; 623/1.11; 623/1.15
(58) Field of Classification Search .............. 623/2.1, 623/2.37, 2.11, 2.36, 1.11, 1.15; 606/108, 606/191, 192, 194, 198; 604/164.01, 164.03, 604/164.12, 170.02
See application file for complete search history.

(56) References Cited

U.S. PATENT DOCUMENTS

| 6,551,303 | B1 * | 4/2003 | Van Tassel et al. ........... 604/508 |
| 6,978,176 | B2 * | 12/2005 | Lattouf ............................. 607/9 |
| 7,585,321 | B2 * | 9/2009 | Cribier ......................... 623/2.14 |
| 2005/0154252 | A1 * | 7/2005 | Sharkey et al. ................. 600/37 |
| 2006/0149368 | A1 * | 7/2006 | Spence ......................... 623/2.37 |
| 2007/0061010 | A1 * | 3/2007 | Hauser et al. ................. 623/2.36 |
| 2009/0018526 | A1 * | 1/2009 | Power et al. .................... 604/508 |
| 2009/0076586 | A1 * | 3/2009 | Hauser et al. ................. 623/1.12 |

FOREIGN PATENT DOCUMENTS

| WO | WO 01/78625 | 10/2001 |
| WO | WO 2005/046520 | 5/2005 |
| WO | WO 2005/102181 | 11/2005 |

OTHER PUBLICATIONS

PCT International Search Report for International Application No. PCT/US2007/078874 dated Jul. 18, 2008.

* cited by examiner

*Primary Examiner* — David Isabella
*Assistant Examiner* — Seema Swaminathan
(74) *Attorney, Agent, or Firm* — David L. Hauser

(57) ABSTRACT

The present disclosure concerns embodiments of a reshaping apparatus and methods for restoring the conical shape of a dilated heart ventricle, or at least reshaping the ventricle to a more conical shape to counter the effects of dilation, thereby improving pumping efficiency. In an exemplary embodiment, a reshaping apparatus comprises an implantable body that can be delivered to a dilated left ventricle via the patient's vasculature in a minimally-invasive procedure. When deployed inside the left ventricle, the body is adapted to apply a longitudinal (downward) force against the inner surface of the left ventricle that causes the ventricle to distend or elongate downwardly relative to the base of the heart so as to at least partially restore the conical shape of the heart. In other embodiments, one or more tension members can be secured to heart tissue inside a heart chamber or on the outside of the heart and placed in tension to reshape the geometry of the heart.

23 Claims, 11 Drawing Sheets

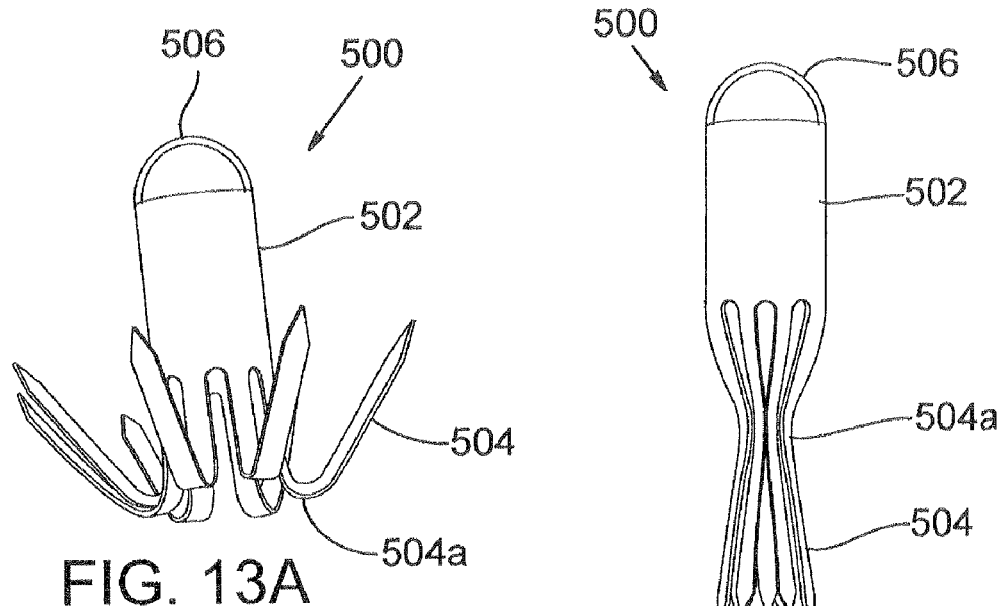
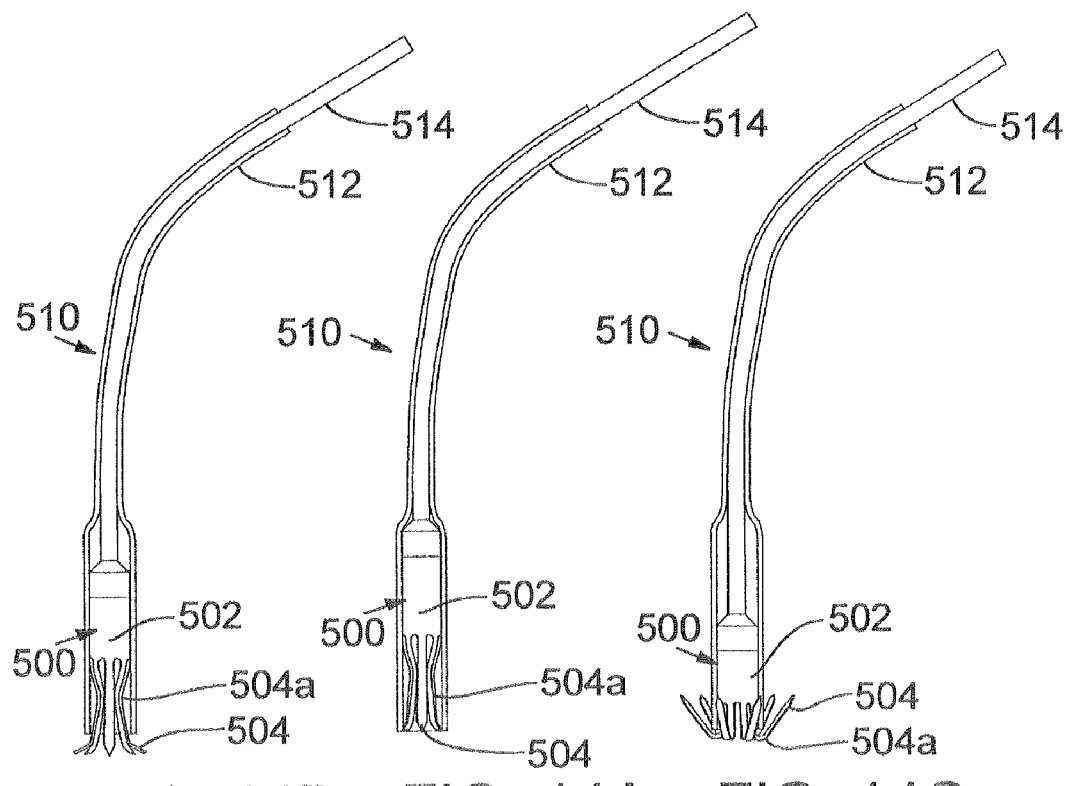

METHOD AND APPARATUS FOR RESHAPING A VENTRICLE

CROSS REFERENCE TO RELATED APPLICATION

The present application claims the benefit of U.S. Provisional Application No. 60/849,242, filed Oct. 4, 2006, which is incorporated herein by reference.

FIELD

The present invention relates to medical devices and methods and, more particularly, to a medical device and method for treating a dilated ventricle.

BACKGROUND

A healthy left ventricle of a human heart, which is the primary pumping chamber, is generally conical or apical in shape in that it is longer (along a longitudinal axis extending in a direction from the aortic valve to the apex) than it is wide (along a transverse axis extending between opposing walls at the widest point of the left ventricle) and descends from a base with a decreasing cross-sectional circumference to a point or apex. The pumping of blood from the left ventricle is accomplished by a squeezing motion and a twisting or torsional motion.

The squeezing motion occurs between the lateral wall of the left ventricle and the septum. The twisting motion is a result of heart muscle fibers that extend in a circular or spiral direction around the heart. When these fibers contract, they produce a gradient of angular displacements of the myocardium from the apex to the base about the longitudinal axis of heart. The resultant force vectors extend at angles from about 30 to 60 degrees to the flow of blood through the aortic valve. The contraction of the heart is manifested as a counterclockwise rotation of the apex relative to the base, when viewed from the apex. A healthy heart can pump blood from the left ventricle in a very efficient manner due to the spiral contractility of the heart.

Chronic congestive heart failure and other disease processes can cause the heart to enlarge or dilate from a conical shape to a shorter and wider shape, which in turn causes the muscle fibers to become reoriented. As a result of the dilation, the orientation of the muscle fibers produces lines of force directed generally laterally of the left ventricle at about 90 degrees relative to the outward flow of the blood. Hence, blood is pushed inwardly (toward the center of the left ventricle), rather than at an acute angle relative to the outward blood flow, thereby greatly reducing the pumping efficiency of the left ventricle. In a similar manner, dilation of the heart also can adversely affect the function of the right ventricle.

A variety of treatment procedures have been proposed over the years for treating left ventricular dilatation. However, these procedures typically involve radical open-heart surgeries designed to surgically reduce the volume of the left ventricle. In recent years, several new minimally invasive techniques for improving heart function have been proposed that do not require opening the chest or cardiopulmonary by-pass. However, none of these procedures has gained widespread acceptance and most fail to address the underlying cause of the problem.

Accordingly, an urgent need exists for a new device and method for treating left ventricular dilatation.

SUMMARY

According to one aspect, the present disclosure concerns embodiments of a reshaping apparatus and methods for restoring the conical shape of a dilated heart ventricle, or at least reshaping the ventricle to a more conical shape to counter the effects of dilation, thereby improving pumping efficiency. In particular embodiments, the left ventricle is reshaped in a non-surgical or minimally-invasive procedure without opening the chest or cardiopulmonary by-pass. The shape of the left ventricle can be altered by applying a longitudinal force to the apex of the left ventricle to move the apex downward (relative to the base of the heart), such as by pushing or pulling the apex downwardly. By applying such a force (i.e., pushing or pulling) on the apex, the left ventricle becomes longer and thinner and thereby achieves a more conical shape. As a result, the muscle fibers are better oriented to accomplish torsional motion of the heart, thereby increasing the efficiency and work capability of the left ventricle. The embodiments disclosed herein can also be used to reshape a dilated right ventricle of the heart.

A reshaping device according to one exemplary embodiment comprises an implantable body that can be delivered to a dilated left ventricle via the patient's vasculature in a minimally-invasive procedure. When deployed inside the left ventricle, the body is adapted to apply a longitudinal (downward) force against the inner surface of the left ventricle that causes the ventricle to distend or elongate downwardly relative to the base of the heart so as to at least partially restore the conical shape of the heart. The body can include a radially compressible and expandable anchor member and an elongated pusher that extends from the anchor member. The anchor member can have a configuration similar to that of a conventional stent and can be deployed within the left ventricular outflow tract, for example just below the aortic valve. Once deployed, the pusher member extends downwardly from the anchor member and has a distal end portion that engages and pushes against the inner surface of the left ventricle.

In one alternative embodiment, the reshaping device may comprise an elongate pusher member and an anchor member configured to apply a lateral force against the surrounding tissue, which is effective to move the anterior leaflet of the mitral valve toward the posterior leaflet for improving leaflet coaption, thereby reducing or eliminating mitral valve regurgitation. In another embodiment, the reshaping device may comprise an elongate pusher member and an anchor member in the form of a prosthetic valve assembly configured for deployment within the aortic annulus. In this embodiment, the reshaping device can be used to replace the function of the aortic valve as well as to reshape the left ventricle to counter the effects of dilation.

In other alternative embodiments, a reshaping apparatus for reshaping a dilated ventricle can include one or more tension members, such as suture lines, that are connected to tissue at opposing locations inside the ventricle. The tension members are placed in tension to pull the opposing walls of the ventricle into closer proximity to reshape the dilated ventricle. For example, each tension member can be a suture loop that extends through tissue at opposite locations on the inner walls of the ventricle. Alternatively, the tension members can be secured to the inner walls of the ventricle using self-deploying anchor members that can be deployed within the ventricle using a delivery catheter. After the anchor members are deployed at predetermined locations within the ventricle, tension members, such as suture lines, call be connected to the anchor members and placed in tension to draw the inner walls of the ventricle into closer proximity.

In one representative embodiment, a device for reshaping a ventricle of a heart comprises anchor means for anchoring the device to tissue inside the heart, and pusher means for applying a pushing force against the inside of the ventricle to cause the apex of the heart to move away from the anchor means to distend the heart in a direction extending from the base of the heart to the apex.

In another representative embodiment, an apparatus for altering a shape of a heart comprises a tension member having first and second end portions. A first anchor member is connected to the first end portion of the tension member and comprises a plurality of radially self-expanding tissue engaging members that are configured to anchor themselves to tissue at a first location inside the heart. A second anchor member is connected to the second end portion of the tension member and comprises a plurality of radially self-expanding tissue engaging members that are configured to anchor themselves to tissue at a second location inside the heart. The tension member is placed in tension between the first and second anchor members such that inner walls of the heart are drawn toward each other to alter a shape of the heart.

In another representative embodiment, a method for reshaping a dilated ventricle of a patient comprises applying a longitudinal force against an apex portion of the ventricle to elongate the ventricle. The force can be applied by deploying a reshaping device inside the dilated ventricle. The reshaping device is configured to apply a pushing force against an inner surface of the ventricle at the apex to cause the ventricle to elongate. Alternatively, the longitudinal force can be applied to the apex portion by securing a first end portion of a tension member to the outer surface of the apex portion and securing a second end portion of the tension member to a body part below the apex portion to draw the apex portion downwardly and toward the body part, thereby elongating the ventricle.

In yet another representative embodiment, a method for reshaping a dilated ventricle of a patient comprises positioning a tension member having first and second ends in the ventricle, securing the first end of the tension member to a first inner wall of the ventricle and securing the second end of the tension member to a second inner wall of the ventricle, and tensioning the tension member to draw the inner walls toward each other.

The foregoing and other features and advantages of the invention will become more apparent from the following detailed description, which proceeds with reference to the accompanying figures.

BRIEF DESCRIPTION OF THE DRAWINGS

FIG. 3 is a side view of an exemplary embodiment of a reshaping device that is implantable in a dilated left ventricle for reshaping the ventricle.

FIGS. 5A-5C are schematic side views showing the reshaping device of FIG. 3 being deployed from a delivery catheter that can be used to deliver the reshaping device to the implantation site via the patient's vasculature, according to one embodiment.

FIG. 13A is a perspective view of an exemplary embodiment of an anchor member for a suture line shown in an expanded state.

FIG. 13B is a perspective view of the anchor member of FIG. 13A shown in a compressed state for delivery to the heart.

FIGS. 14A-14C illustrate an exemplary embodiment of a delivery catheter being used to deploy the anchor member of FIGS. 13A and 13B.

DETAILED DESCRIPTION

As used herein, the singular forms "a," "an," and "the" refer to one or more than one, unless the context clearly dictates otherwise.

As used herein, the term "includes" means "comprises." For example, a device that includes or comprises A and B contains A and B but may optionally contain C or other components other than A and B. A device that includes or comprises A or B may contain A or B or A and B, and optionally one or more other components such as C.

Figure 1:
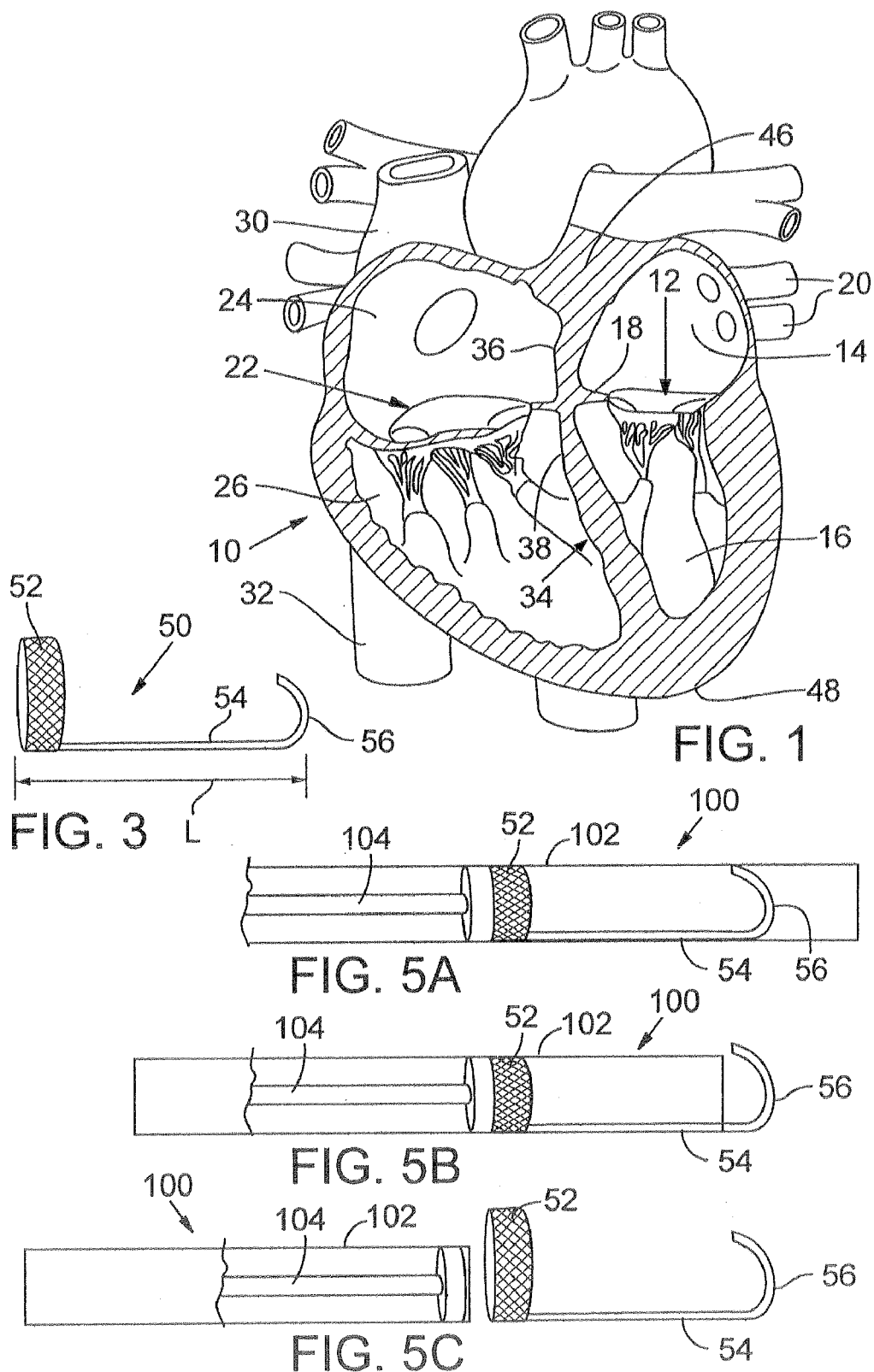
FIG. 1 illustrates a cross-sectional view of a heart for background purposes.
Figure 4:
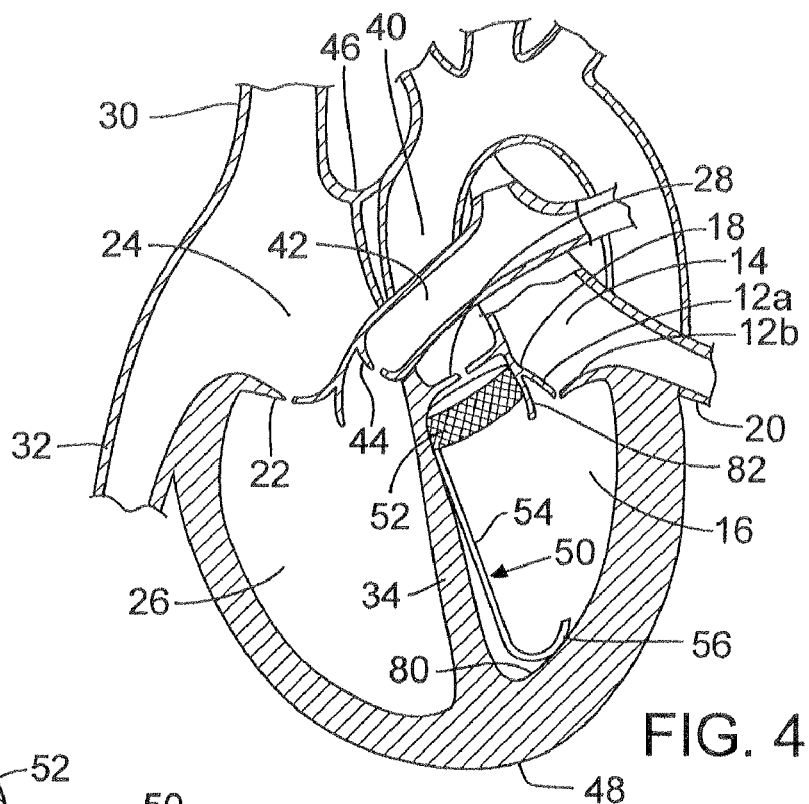
FIG. 4 is a cross-sectional view of a heart showing the reshaping device shown in FIG. 3 deployed in the left ventricle.

With reference to FIGS. 1 and 4, a four-chambered heart 10 is illustrated for background purposes. On the left side of the heart, the mitral valve 12 is located between the left atrium 14 and left ventricle 16. The mitral valve generally comprises two leaflets; an anterior leaflet 12a and a posterior leaflet 12b. The mitral valve leaflets are attached to a mitral valve annulus 18, which is defined as the portion of tissue surrounding the mitral valve orifice. The left atrium 14 receives oxygenated blood from the pulmonary veins 20. The oxygenated blood that is collected in the left atrium 14 enters the left ventricle 16 through the mitral valve 12.

Contraction of the left ventricle 16 forces blood through the left ventricular outflow tract and into the aorta 40 (FIG. 4). The aortic valve 28 is located between the left ventricle 16 and the aorta 40 for ensuring that blood flows in only one direction (i.e., from the left ventricle to the aorta). As used herein, the left ventricular outflow tract (LVOT) is intended to generally include the portion of the heart through which blood is channeled from the left ventricle to the aorta. The LVOT shall include the aortic valve annulus and the adjacent region extending directly below the aortic valve annulus and the portion of the ascending aorta adjacent the aortic valve.

As best shown in FIG. 1, on the right side of the heart, the tricuspid valve 22 is located between the right atrium 24 and the right ventricle 26. The right atrium 24 receives blood from the superior vena cava 30 and the inferior vena cava 32. The superior vena cava 30 returns de-oxygenated blood from the upper part of the body and the inferior vena cava 32 returns de-oxygenated blood from the lower part of the body. The right atrium 24 also receives blood from the heart muscle itself via the coronary sinus. The blood in the right atrium 24 enters into the right ventricle 26 through the tricuspid valve 22. Contraction of the right ventricle forces blood through the right ventricular outflow tract and into the pulmonary arteries. The pulmonic valve 44 (FIG. 4) is located between the right ventricle 26 and the pulmonary trunk 42 for ensuring that blood flows in only one direction from the right ventricle to the pulmonary trunk. The blood enters the lungs for oxygenation and is returned to the left atrium 16 via the pulmonary veins 20.

The left and right sides of the heart are separated by a wall generally referred to as the septum 34. The portion of the septum that separates the two upper chambers (the right and left atria) of the heart is termed the atrial (or interatrial) septum 36 while the portion of the septum that lies between the two lower chambers (the right and left ventricles) of the heart is called the ventricular (or interventricular) septum 38. As shown in FIGS. 1 and 4, a healthy heart has a generally conical shape that tapers from a base 46 to an apex 48.

Figure 2:
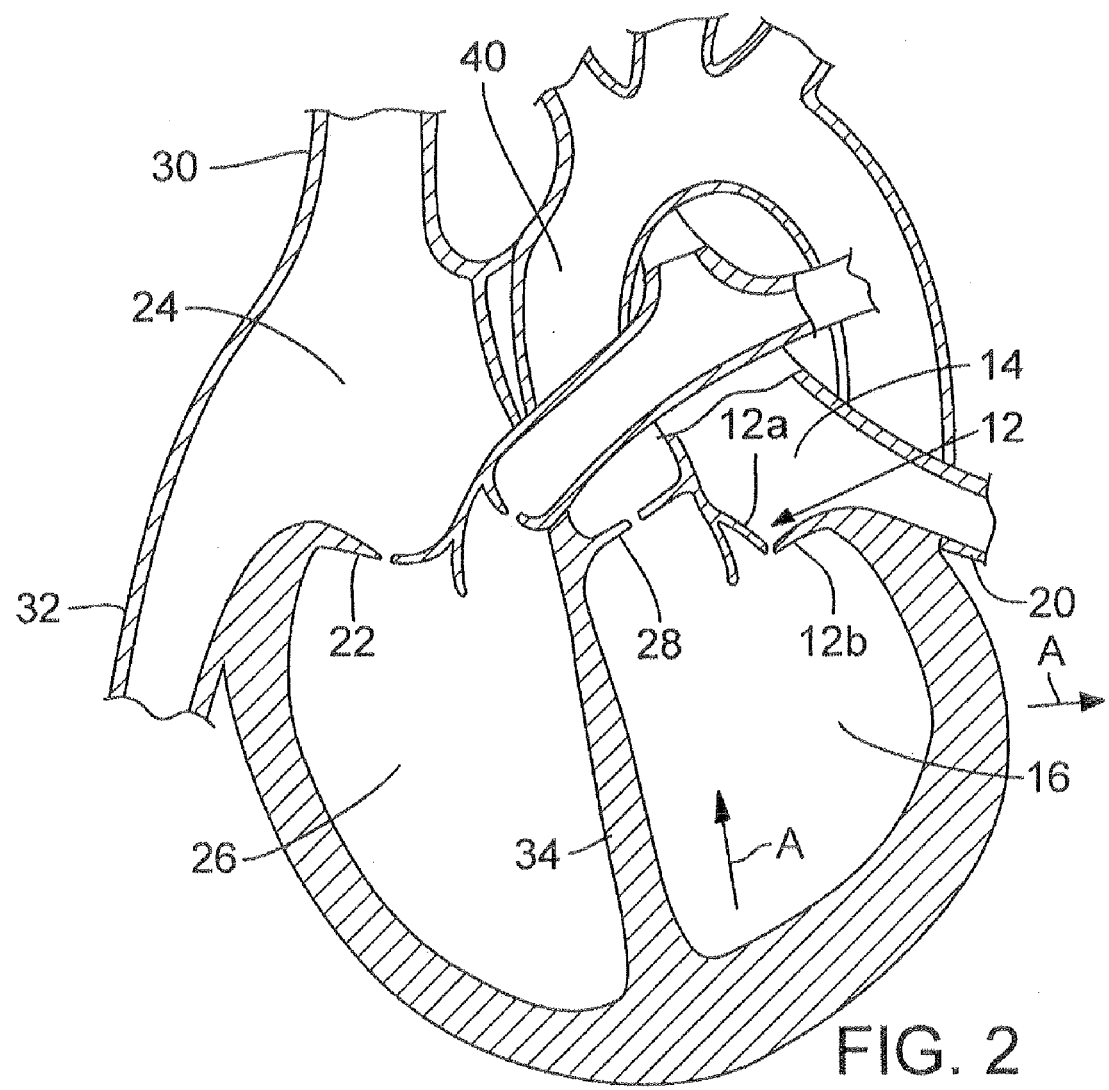
FIG. 2 illustrates a cross-sectional view of a heart having a dilated left ventricle.

As discussed above, heart disease can cause dilation of the heart, resulting in greatly reduced pumping efficiency of the left ventricle. As depicted in FIG. 2, dilatation causes the posterior wall of the left ventricle to distend outward and the apex to move upward, as generally shown by arrows A. The dilatation results in a left ventricle having an undesirable round shape, as generally shown in FIG. 2. Heart disease can also cause dilation of the other chambers of the heart.

According to one aspect, the present disclosure concerns embodiments of a reshaping apparatus and methods for restoring the conical shape of a dilated left ventricle, or at least reshaping the left ventricle to a more conical shape to improve pumping efficiency. In particular embodiments, the left ventricle is reshaped in a non-surgical or minimally-invasive procedure without opening the chest or cardiopulmonary by-pass. The shape of the left ventricle can be altered by applying a longitudinal force to the apex of the left ventricle to move the apex downward (relative to the base of the heart), such as by pushing or pulling the apex downwardly. By applying such a force (i.e., pushing or pulling) on the apex, the left ventricle becomes longer and thinner and thereby achieves a more conical shape. As a result, the muscle fibers are better oriented to accomplish torsional motion of the heart, thereby increasing the efficiency and work capability of the left ventricle. The embodiments disclosed herein can also be used to reshape the right ventricle of the heart.

With reference to FIG. 3, an exemplary embodiment of a reshaping device 50 for reshaping a left ventricle is now shown for purposes of illustration. The device 50 is configured for deployment within a left ventricle and generally comprises a body having an anchor member 52 and an elongate pusher member, or arm, 54 mounted to the anchor member 52. The pusher member 54 in the illustrated embodiment is a substantially J-shaped member having a proximal end connected to the anchor member and an arcuate, atraumatic flexible tip portion 56 shaped for engagement with the inner surface of the left ventricle. The pusher member 54 is configured for pushing against the inner surface of the left ventricle after the device 50 is deployed in the left ventricle, as further described below.

The pusher member 52 is preferably formed from a round wire or a generally flat, ribbon-like piece of material. Alternatively, the pusher member 52 can comprise an elongated tubular body that can be formed from a mesh material, such as used to form stents, or a solid (non-perforated) material. The pusher member 50 can be made of any suitable biocompatible material, such as, for example, stainless steel or a polymer.

In the illustrated embodiment, the anchor member 52 takes the form of a radially compressible and expandable stent that is adapted to expand to a size sufficient to engage adjacent tissue in the heart and anchor the device firmly in place. The anchor member 52 can include various attachment elements (not shown), such as barbs, staples, flanges, and the like for enhancing the ability of the anchor member to anchor to the surrounding tissue. In one specific implementation, for example, the anchor member 52 can be sized for deployment within the left ventricular outflow tract, such as at a location just beneath the aortic valve. In another implementation, the anchor member 52 can be configured for deployment within the mitral valve annulus, within the aortic valve annulus, or within the left atrium.

The anchor member 52 can be a self-expanding or balloon-expandable stent. When a self-expanding stent is used, the stent can be formed from a shape memory material, such as, for example, Nitinol, and can be delivered using a sheath. After reaching the treatment site, the device 50 is advanced out of the distal end of the sheath and the stent 52 expands into contact with the surrounding tissue. When in the form of a balloon-expandable stent, the stent can be formed from stainless steel or any of various other suitable materials. The balloon-expandable stent 52 can be configured to be crimped to a reduced diameter and placed over a deflated balloon on the distal end portion of an elongate balloon catheter.

FIG. 4 shows the device 50 deployed in the left ventricle 16. As shown, the anchor member 52 is deployed in the left ventricular outflow tract just below the aortic valve 28 and the tip portion 56 of the pusher member 54 engages an inferior inner surface portion 80 of the left ventricle. The overall length L (FIG. 3) of the device 50 when deployed is selected such that the tip portion 56 pushes downwardly against the inner surface 80 while the anchor member 52 is secured firmly in place below the aortic valve 28. The force applied by the pusher member 54 causes the left ventricle 16 to distend or elongate longitudinally in a direction extending from the base 46 to the apex 48. When compared with FIG. 2, it can be seen that the device 50 has reshaped the left ventricle to provide it with a more conical shape. As described above, the resulting conical shape improves the pumping efficiency of the heart. The device also can be configured to be deployed in a dilated right ventricle 26 for reshaping the right ventricle in an analogous procedure.

The overall length L of the device 50 can be selected to achieve a desired reshaping of the left ventricle. Increasing the length L of the device 50 will increase the change in length of the left ventricle between the aortic valve and the apex while decreasing the length L of the device 50 will decrease the change in length of the left ventricle.

The anchor member 52 can also be used to help treat mitral valve regurgitation. Regurgitation through the mitral valve 12 occurs when the mitral valve fails to close properly, allowing blood from the left ventricle 16 to leak into the left atrium 14. Regurgitation typically is caused by changes in the geometric configurations of the left ventricle, papillary muscles, and the mitral valve annulus. As shown in FIG. 4, the anchor member 52 can be sized to engage tissue 82 extending from the aortic valve adjacent the anterior portion of the mitral valve 12. When the anchor member 52 is deployed, it applies a lateral force against the tissue 82. This force urges the anterior leaflet 12a toward the posterior leaflet 12b for improving leaflet coaption, thereby reducing or eliminating mitral valve regurgitation.

FIGS. 5A-5C schematically illustrate an exemplary embodiment of a delivery catheter 100 for delivering and deploying the device 50 in the left ventricle. The catheter 100 in the illustrated embodiment is adapted to be used with a device 50 that has a radially self-expandable anchor member 52. The apparatus 100 includes an elongated delivery sheath 102 (the distal end portion of which is shown in FIGS. 5A-5C) and a pusher member, or advancing member, 104 slidably received in the lumen of the deliver sheath 102.

The catheter 100 can be introduced percutaneously into the patient's vasculature (e.g., into a peripheral artery such as the femoral artery) and advanced to the implantation site. In certain embodiments, for example, the catheter is sized for insertion through a small incision in the groin and has a length of at least about 80 cm, preferably about 90 to 100 cm, to allow transluminal positioning of the shaft from the femoral and iliac arteries to the ascending aorta in a retrograde approach. Alternatively, the catheter may have a shorter length, e.g. about 20 to 60 cm, for introduction through the iliac artery, through the brachial artery, through the carotid or subclavian arteries, or through a penetration in the aorta itself. In the femoral approach, the catheter desirably is long enough and flexible enough to traverse the path through the femoral artery, iliac artery, descending aorta and aortic arch. At the same time, the catheter desirably has sufficient pushability to be advanced to the ascending aorta by pushing on the proximal end, and has sufficient axial, bending, and torsional stiffness to allow the physician to control the position of the distal end, even when the catheter is in a tortuous vascular structure. Alternatively, the catheter may be passed through a port between ribs in the patient's thorax above the heart and through an incision in the aortic arch, in a so-called minimally-invasive procedure.

As shown in FIG. 5A, during advancement to the left ventricle, the device 50 is initially contained within the delivery sheath 102 with the anchor member 52 retained in a radially compressed state. In the retrograde approach, the distal portion of the delivery sheath 102 is advanced through the aorta 40 (FIG. 4), across the aortic valve 28 and into the left ventricle 16 to position the sheath distal end adjacent the inner surface 80 of the left ventricle. Once properly positioned, the sheath 102 is retracted relative to the pusher member 104 and the device 50 to expose the curved tip portion 56, as shown in FIG. 5B. The operator pushes the tip portion 56 firmly against the surface 80 to distend the left ventricle and to position the anchor member 52 in a deployment position below the aortic valve 28. As depicted in FIG. 5C, the sheath 102 can then be withdrawn further to advance the anchor member 52 through the distal end of the sheath, thereby allowing the anchor member 52 to expand into contact with the surrounding tissue to retain the device firmly in place with the tip portion 56 bearing against the inner surface 80.

Figure 6A:
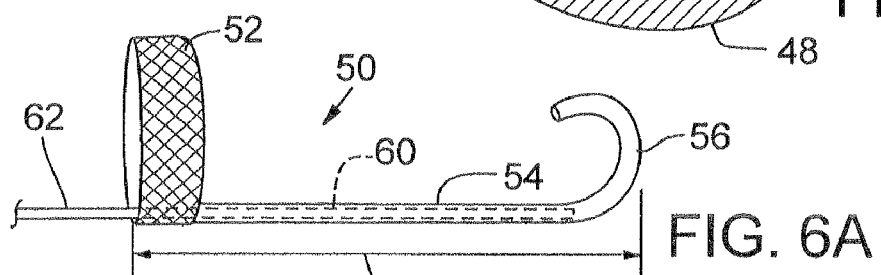
FIGS. 6A-6C are side views of a variation of the embodiment of FIG. 3 illustrating a technique for adjusting the overall length of the reshaping device.
Figure 6B:
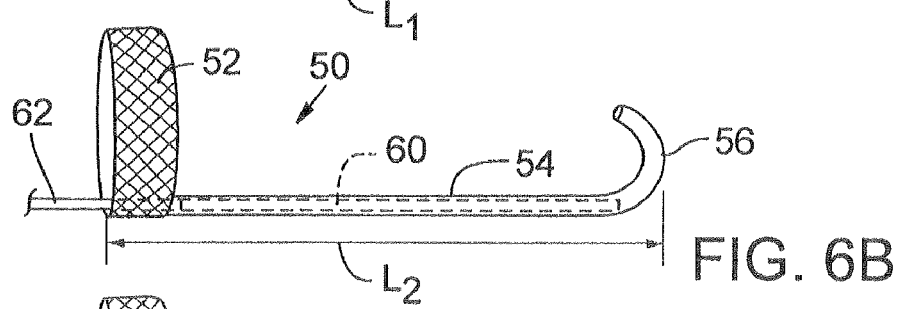
Figure 6C:
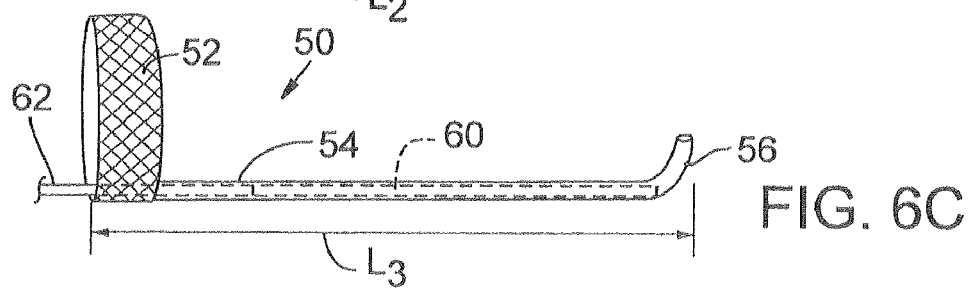

The pusher member 54 of the reshaping device 50 can be configured to have a variable or adjustable length to achieve a desired reshaping of the left ventricle. For example, as illustrated in FIGS. 6A-6B, the pusher member 54 can have an inner lumen that receives a dowel or stylet 60 that is slidable within lumen. The stylet 60 is preferably a substantially rigid member that can resist bending or flexing when the device is deployed in the heart. The stylet 60 can be inserted into and withdrawn from the tip portion 56 to adjust the overall length of the device 50. In FIG. 6A, for example, the device has an overall length $L_1$. As the stylet 60 is inserted into the tip portion 56, as shown in FIG. 6B, the stylet 60 straightens a segment of the tip portion 56 to increase the overall length of the device to a length $L_2$. The stylet 60 can be further advanced into the tip portion 56 to increase the overall length of the device to a greater length $L_3$. Conversely, withdrawing the stylet 60 from the tip portion 60 allows the segment of the tip portion that does not contain the stylet to assume a curved shape, thereby shortening the overall length of the device. A detachable, elongated control member 62, such as a wire, can be attached to the proximal end of the stylet 60 for moving the stylet relative the pusher member 54. The control member 62 can have a proximal end located outside the patient to allow the surgeon to adjust the length of the reshaping device after the device is deployed in the heart.

Figure 7:
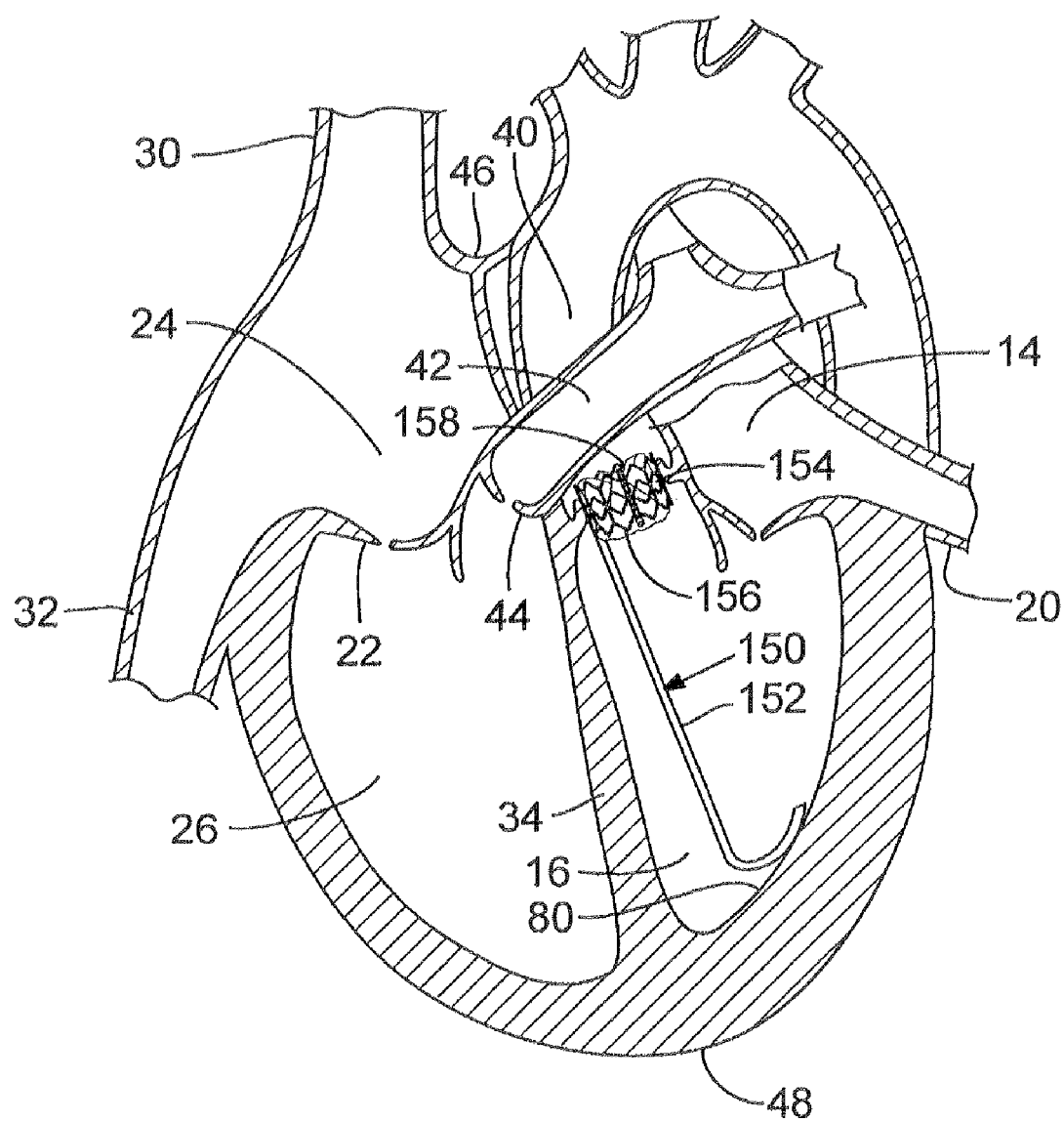
FIG. 7 is a cross-sectional view of a heart showing another exemplary embodiment of a reshaping device incorporating a prosthetic aortic valve that is deployed within the native aortic valve.

FIG. 7 shows another embodiment of an implantable reshaping device, indicated at 150. The reshaping device 150 includes a pusher member 152 and an anchor member 154 that comprises a prosthetic valve assembly. The valve assembly 154 comprises a radially compressible and expandable stent, or frame, 156 that mounts a flexible valve member 158. The stent 156 and valve member 158 can be deployed within the aortic annulus to replace the function of the native valve. Thus, in this embodiment, the stent 156 serves the dual functions of anchoring the reshaping device 150 in place for reshaping the left ventricle and supporting the valve member 158. Once deployed, the pusher member 152 applies a longitudinally directed force against the inner surface 80 of the left ventricle, forcing the apex 48 to move downwardly relative to the base 48 to counter the effects of dilation.

The stent 156 in the illustrated embodiment comprises a plurality of angularly-spaced axial struts, or support members, that extend axially (longitudinally) of the stent. The stent 156 can also include a plurality of axially-spaced, circumferential bands, or struts, attached to the axial struts. The circumferential struts are formed with multiple bends that allow the stent to be compressed to a smaller diameter for delivery to an implantation site and expanded to its functional size for anchoring the valve assembly to the native valve tissue. For example, each of the circumferential struts in the illustrated configuration includes a plurality of linear strut members arranged in a zig-zag or saw-tooth configuration defining bends between adjacent strut members.

In alternative embodiments, the stent can have other configurations. For example, one or more of the circumferential bands can have a curved or serpentine shape rather than a zig-zag shape. Further, the stent can include various attachment elements (not shown), such as barbs, staples, flanges, and the like for enhancing the ability of the stent to anchor to the surrounding tissue.

The valve member 158 can have a leafed-valve configuration, such as a tricuspid valve configuration. The valve member 158 can be formed from three pieces of pliant material connected to each other at seams aligned with axial struts of the frame 156 to form collapsible leaflets. The valve member 158 can be made from biological matter, such as natural tissue, pericardial tissue (such as bovine, porcine or equine pericardium), a harvested natural valve or other biological tissue. Alternatively, the valve member 158 can be made from biocompatible polymers or similar materials.

Various other self-expanding and balloon expandable prosthetic valve configurations also can be used. Additional details regarding other valves that can be utilized are disclosed in U.S. Pat. No. 5,411,552; U.S. Pat. No. 6,730,118 and U.S. Publication No. 2004/0186563, which are incorporated herein by reference.

Figure 8:
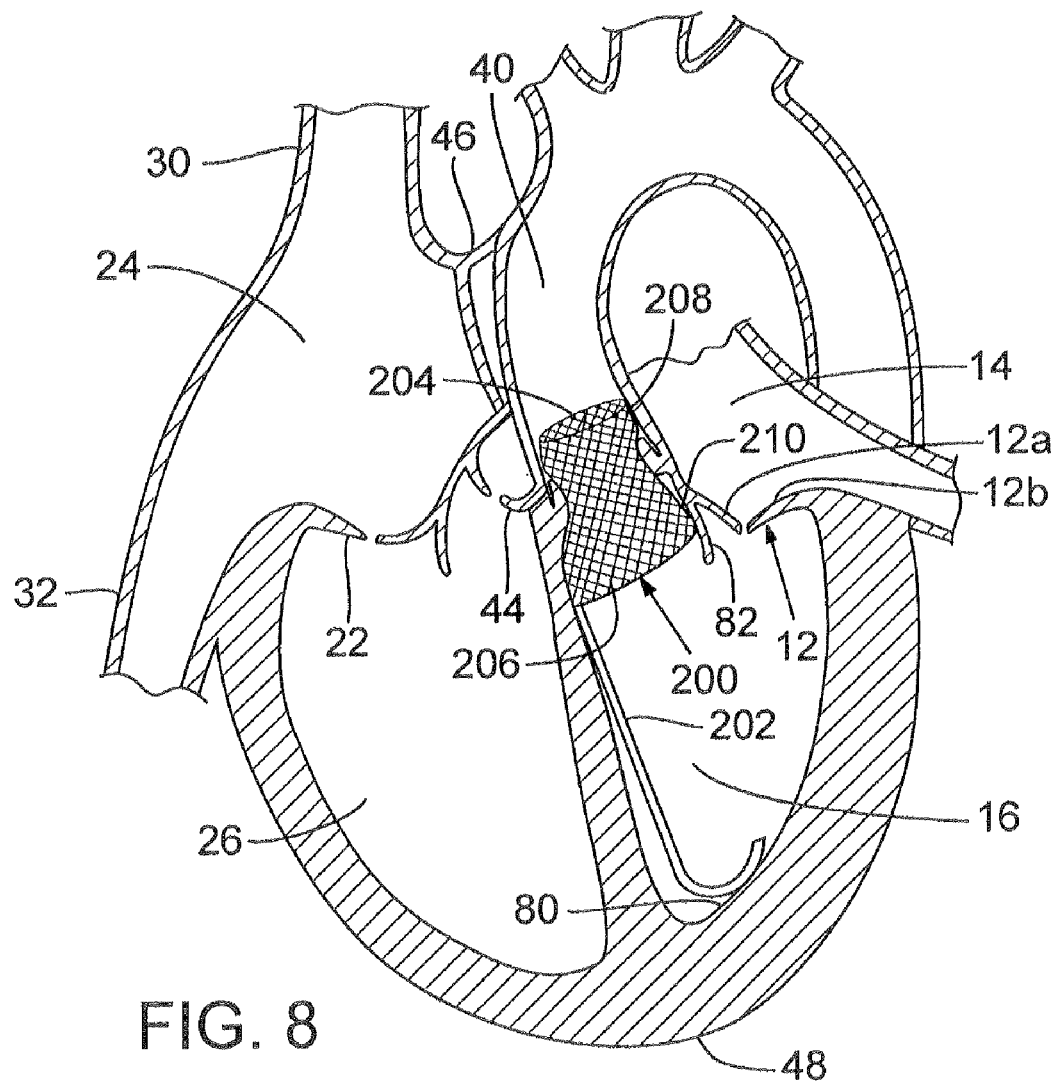
FIG. 8 is a cross-sectional view of a heart showing another exemplary embodiment of a reshaping device incorporating a prosthetic aortic valve that is deployed within the native aortic valve and is adapted to provide a lateral force against the anterior mitral valve leaflet to improve leaflet coaptation.

In yet another embodiment, as shown in FIG. 8, a reshaping device 200 comprises a pusher member 202 connected to a prosthetic valve assembly 204. The valve assembly 204 includes an outer frame or stent 206 that mounts a flexible valve member (not shown). In this embodiment, the stent 206 has a generally tubular upper portion 208 that is deployed in the aortic annulus and a flared or enlarged lower portion 210 that extends below the aortic annulus and has a larger diameter. The lower portion may be sized for engaging and applying a lateral force to the tissue 82 below the aortic annulus, thereby urging the anterior mitral valve leaflet 12a toward the posterior leaflet 12b to improve leaflet coaption. In this embodiment, the flexible valve member may be mounted to the stent 206 within the tubular upper portion 208, preferably adjacent to the native aortic valve. Alternatively, the flexible valve member may be mounted to the stent within the enlarged lower portion, wherein the valve assembly may have a larger diameter and greater flow area. Although the prosthetic valve assembly in FIG. 8 is described as comprising a portion of a reshaping device for treating the left ventricle, alternative embodiments of the prosthetic valve assembly may also be configured for use in alternative applications. For example, the flared stent may be used solely as a replacement valve (i.e., without a pusher member) configured to support a valve member in the enlarged lower portion 210. As described above, such a configuration provides a prosthetic valve having a valve member with a larger flow area for improving blood flow through the heart. Additional details regarding a prosthetic valve assembly having a flared stent suitable for use with the above embodiments can be found in Applicant's co-pending U.S. Publication No. 2007/0061010.

In alternative embodiments, a reshaping device can include a prosthetic mitral valve connected to an elongated pusher member. The prosthetic mitral valve is deployed within the mitral valve annulus of a dilated heart and the pusher member extends downwardly therefrom and applies a force against the inner surface 80 to distend the left ventricle. The prosthetic valve therefore replaces the function of the native valve and serves as an anchor member for securing the reshaping device in place.

In other embodiments, other types of prostheses that are deployable in the mitral valve or in the left atrium for treating mitral valve regurgitation can be mounted to a reshaping device. Such prostheses can serve the additional function of anchoring the reshaping device in place. Details regarding the structure and use of various embodiments of prosthesis for treating a mitral valve can be found in Applicant's copending U.S. Publication No. 2006/0058871 and U.S. Publication No. 2006/0241745, the contents of which are hereby incorporated by reference.

In certain embodiments, apparatuses for reshaping a ventricle can comprise suture lines or other tension members that pull the walls of the left ventricle into closer proximity, thereby countering the effects of heart dilation. In one implementation, for example, a suture loop extends transversely across the left ventricle and through tissue at opposing locations in the ventricle for pulling the ventricle walls closer together.

Figure 9A:
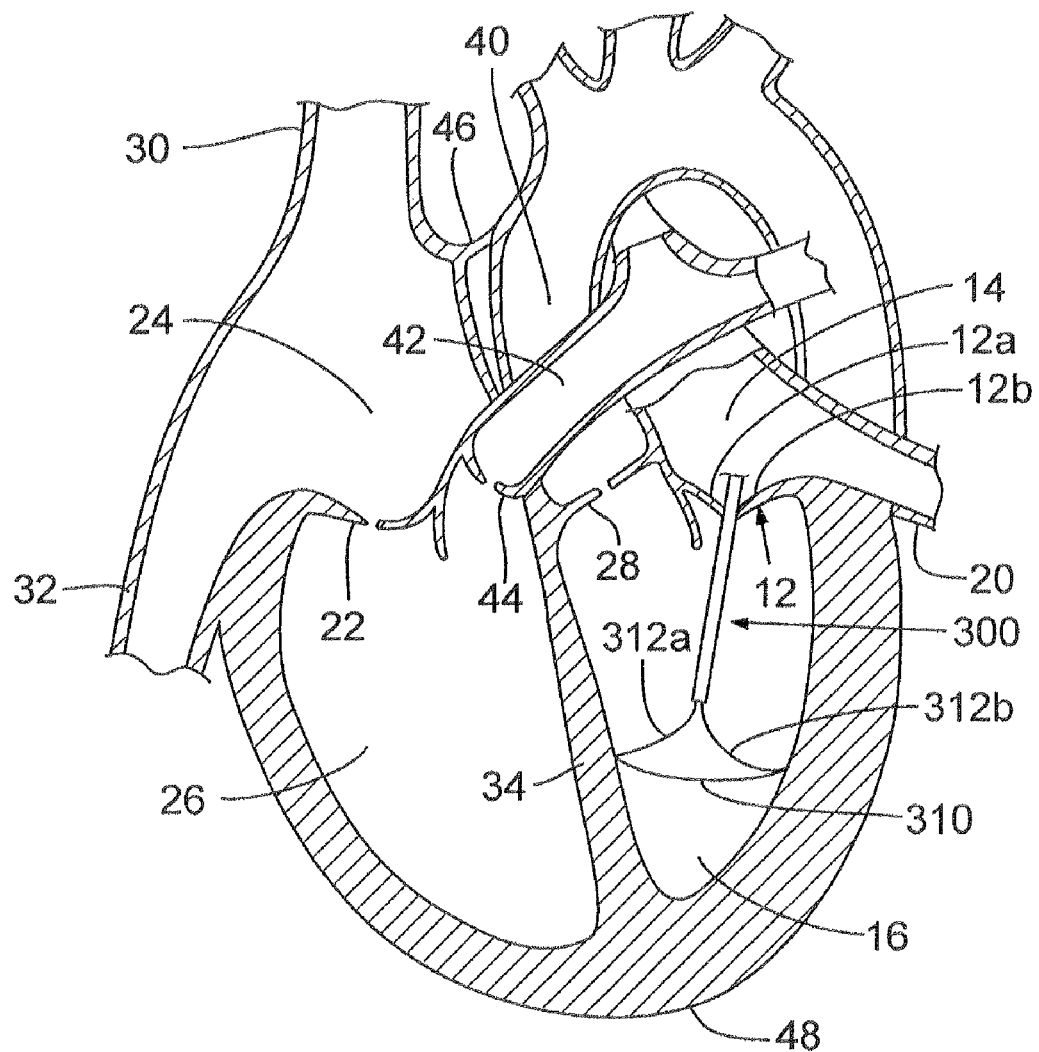
FIGS. 9A and 9B are cross-sectional views of a heart illustrating a technique for securing a suture loop to the inner walls of the left ventricle for reshaping the ventricle.
Figure 9B:
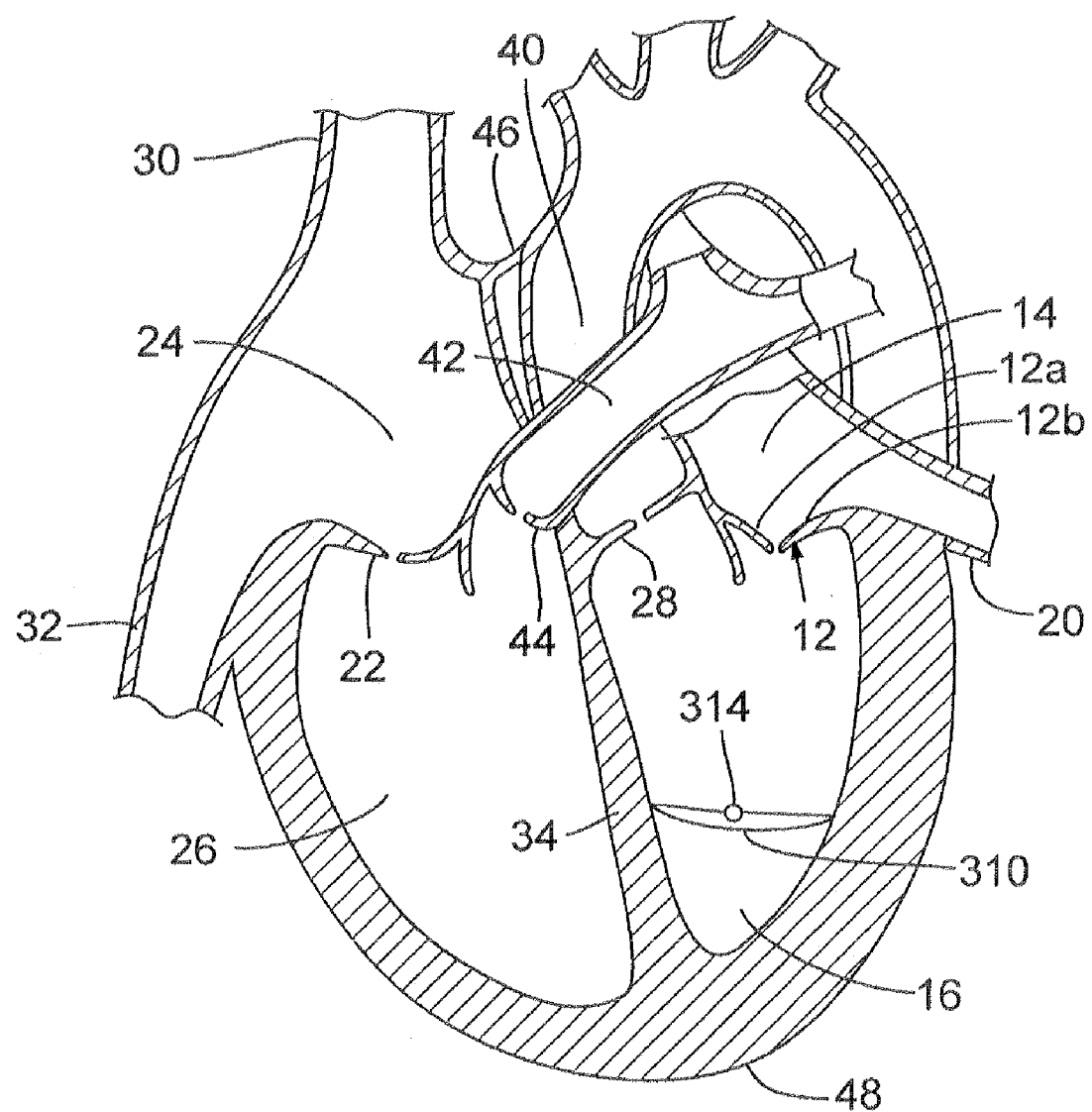

FIG. 9A shows an exemplary embodiment of a catheter 300 that can be used to apply a suture loop 310 to tissue inside the left ventricle in a minimally invasive procedure. Details regarding the structure and use of the catheter 300 are disclosed in Applicant's co-pending U.S. Publication No. 2004/0181238, which is incorporated herein by reference. The catheter 300 can be advanced through the patient's vasculature until its distal end portion is positioned in the left ventricle. The distal end portion of the catheter is placed against a wall of the left ventricle, such as at a location on the septum 34, and a needle is advanced from the catheter and through the tissue for advancing a length of suture through the tissue. The distal end portion of the catheter is then placed against an opposing wall of the left ventricle, and another needle is advanced from the catheter and through the tissue for advancing another length of suture through the tissue, and thus forming the suture loop 310 extending through tissue of opposing walls of the left ventricle. The end portions 312a, 312b of the suture loop still connected to the catheter 300 are pulled taught to pull the opposing walls of the left ventricle toward each other to reshape the left ventricle from a generally round, dilated shape to a more conical shape. A fastener or connector 314 (FIG. 9B) can be advanced from the catheter 300 and over the end portions 312a, 312b to secure the end portions together. The remaining suture leads extending from the connector 314 can then be cut using a cutting member in the catheter 300, thus forming the loop 310 shown in FIG. 9B. Additional suture loops can be applied at other locations in the left ventricle to assist reshaping the left ventricle. For example, one or more suture loops can be formed above or below the suture loop 310 or at the same position as the suture loop 310.

Figure 10:
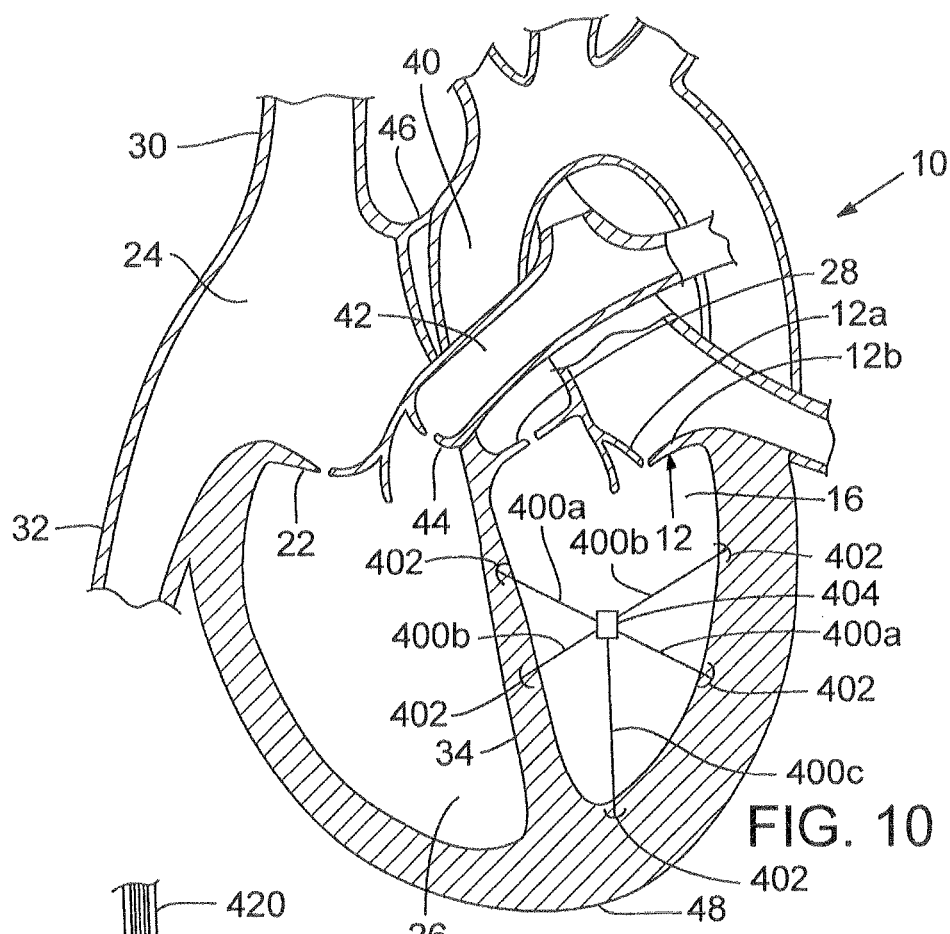
FIG. 10 is a cross-sectional view of a heart showing a reshaping device comprising plurality of tension members secured to the inner walls of the left ventricle for reshaping the ventricle, according to another embodiment.

In another embodiment, apparatus for reshaping a ventricle comprises one or more tension members, such as one or more suture lines, that are connected to tissue at opposing locations inside the ventricle using anchor members that engage the myocardium of the ventricle. For example, with reference to FIG. 10, a reshaping apparatus comprises tension members 400a, 400b, 400c secured to the ventricle walls using anchor members 402. A fastener or clip 404 can be provided for attaching the tension members together at a location within the left ventricle. The tension members are placed in tension between the respective anchor members and the fastener to draw the walls of the left ventricle inward to reshape the left ventricle.

The tension members can be made of any suitable biocompatible material, such as traditional suture material. The tension members in some embodiments can be made of an elastomeric material, such as polyurethane.

In one method of delivering the tension members 400 and the anchor members 402, a catheter is advanced through the patient's vasculature to position the distal end portion of the catheter inside the left ventricle. A deployment mechanism of the catheter is used to deploy the anchor members 402 at selected locations on the inner walls of the left ventricle. When advanced from the catheter, engaging elements of the anchor members 402 deploy and embed themselves in the myocardium, thereby securing the anchor members in place. The catheter can then be used to attach tension members 400 to the anchor members 402 and place the tension members in tension so as to draw the opposing walls of the left ventricle toward each other.

Figure 11:
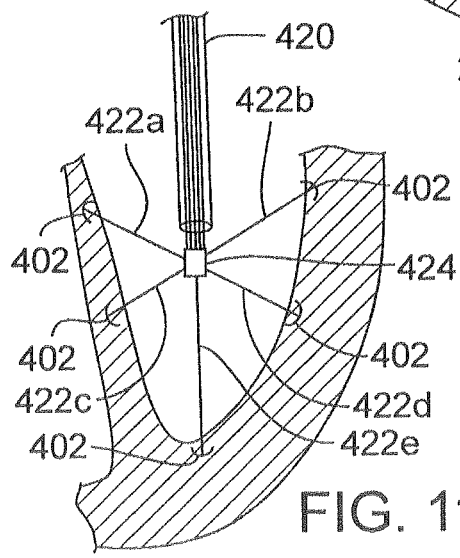
FIG. 11 is a partial, cross-sectional view of a left ventricle showing a catheter being used to secure suture lines to anchor members secured to the inner walls of the left ventricle.

FIG. 11 schematically illustrates a method of using a catheter 420 for securing suture lines to anchor members 402. As shown, a respective suture line 422a, 422b, 422c, 422d, 422e can be secured to each anchor member 402. The suture lines can extend through the catheter to a location outside the body or to a tension-control mechanism of the catheter. The tension in the suture lines can be adjusted as desired for reshaping the left ventricle, such as by manually pulling on the suture lines or by operating the tension-control mechanism. When sufficiently reshaped, a clip 424 can be advanced out of the distal end of the catheter 420 and over the suture lines to secure the suture lines together. The remaining portions of the suture lines are cut and removed and the catheter is then removed from the body.

Figure 12:
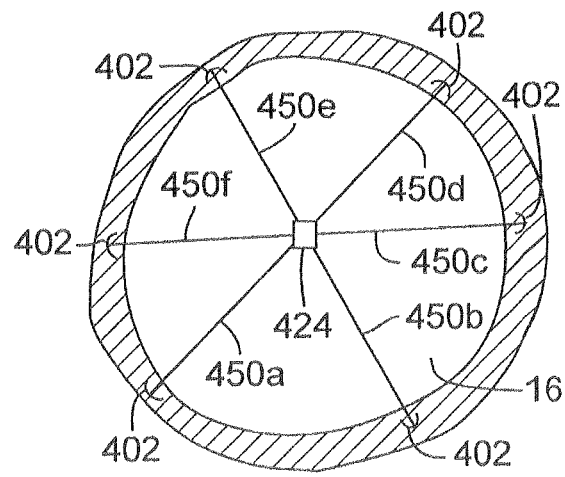
FIG. 12 is a transverse cross-sectional view of a left ventricle showing a plurality of suture lines placed in tension across the ventricle for reshaping the ventricle.

FIG. 12 illustrates another method of placing anchor members 402 in the left ventricle. A transverse cross-section of a left ventricle 16 is shown in FIG. 12. In this embodiment, anchor members 402 are deployed at angularly spaced locations around the inner circumference of the left ventricle. A respective suture line 450a, 450b, 450c, 450d, 450e, 450f is secured to each anchor member 402 and to a fastener 424 at the center of the left ventricle. The suture lines are placed in tension between the anchor members 402 and the fastener 424 to draw the walls of the left ventricle inwardly toward each other. The anchor members 402 can be equally spaced around the inner surface as shown to equally disperse the pulling forces on the inner walls of the left ventricle.

With reference to FIGS. 13A and 13B, an exemplary embodiment of an anchor member 500 is described in detail. The anchor member 500 in the illustrated embodiment comprises a tubular body 502 having a plurality of elongated prongs, or tissue-engaging members, 504 located at a first end thereof and a coupling member 506 located at a second end thereof. In the illustrated embodiment, the coupling member 506 takes the form of a loop.

The elongated prongs 504 are desirably configured to self-expand from the compressed configuration of FIG. 13B to a "flowered" or expanded configuration of FIG. 13A. This flowering is desirably achieved with a self curving area 504a that deflects the prongs 504 radially outward from the center of the body 502 and rearward toward the second end of the body. The prongs 504 are desirably pointed or barbed to facilitate penetration and engagement with the muscular wall of the heart.

The anchor member 500 can be formed from a single tube of shape memory material, such as, for example, Nitinol. During manufacture, the shape memory material may be cut using a mechanical or laser cutting tool. After cutting the tube, the expanded or flowered shape can be imparted to the memory of the shape memory material with techniques known in the art (e.g. heat setting the shape). Methods for manufacturing the anchor member are described in detail in Applicant's co-pending U.S. Provisional Application No. 60/801,446, which is incorporated herein by reference. In one preferred construction, the anchor member can be formed to have an expanded configuration that conforms to the contours of the particular surface area of the heart where the anchor member is to be deployed.

The surface of the anchor member 500, including the prongs 504, is desirably configured to promote tissue growth onto and even into its surface. In one example this growth is achieved by providing the anchor member with a relatively rough and/or porous surface. Additionally, biological coatings of the types known in the art can be included on the surface of the anchor member 500 to promote healing and tissue growth.

FIGS. 14A-14C illustrate an exemplary method of deploying the anchor member 500 using a delivery catheter 510. As shown in FIG. 14A, the anchor member 500 is disposed in the distal end portion of an outer sheath 512 of the delivery catheter 510. A pusher member, or shaft, 514 extends coaxially through the deliver sheath 512 and has a distal end in contact with the anchor member 500. The anchor member and pusher member are slidably received within the outer sheath 512. The outer sheath maintains the anchor member in a compressed configuration during delivery to the implantation site.

The anchor member 500 can be delivered to the heart percutaneously in a retrograde or antegrade approach, or alternatively, it can be inserted through an incision in the chest, through the cardiac tissue and into the left ventricle. When the anchor member is properly positioned at a desired target location within the left ventricle, the outer sheath 512 is retracted relative to the pusher member 514 and the anchor member 500, as illustrated in FIGS. 14B and 14C. As the anchor member 500 advances from the open end of the sheath, the prongs 504 expand outwardly. In certain embodiments, the expansion of the prongs advantageously pulls the anchor member 500 out of the sheath 512.

As the prongs 504 exit the outer sheath 512, the prongs 204 expand, bending back towards the body 202 while grabbing nearby heart tissue. The action of the prongs engaging and embedding themselves in the tissue maintains the anchor member 500 in a stable position within the heart and resists against movement from heart beats, blood flow, and similar actions. In this respect, the anchor member 500 "self-deploys" within the heart, requiring little or no extra pressure from the delivery device 510 to anchor within the muscular wall of the heart.

After implantation in the heart, tissue grows over the anchor member 500, preferably leaving only the coupling member 506 exposed within the left ventricle. It has been found that adequate tissue growth over the anchor member 500 can occur in two or three weeks. However, the amount of time required may depend on various factors such as the particular deployment location of the anchor member 500, the surface features or coatings of the anchor member 500, and/or the condition of the patient.

The coupling member 506 provides a point of attachment for connecting a tension member. A tension member can be connected to an anchor member immediately following deployment of the anchor member in the heart. Alternatively, in some cases, it may be desirable to allow for a suitable time period for tissue to grow over the anchor member before a tension member is connected to the coupling member 506 of the anchor member.

Figure 15:
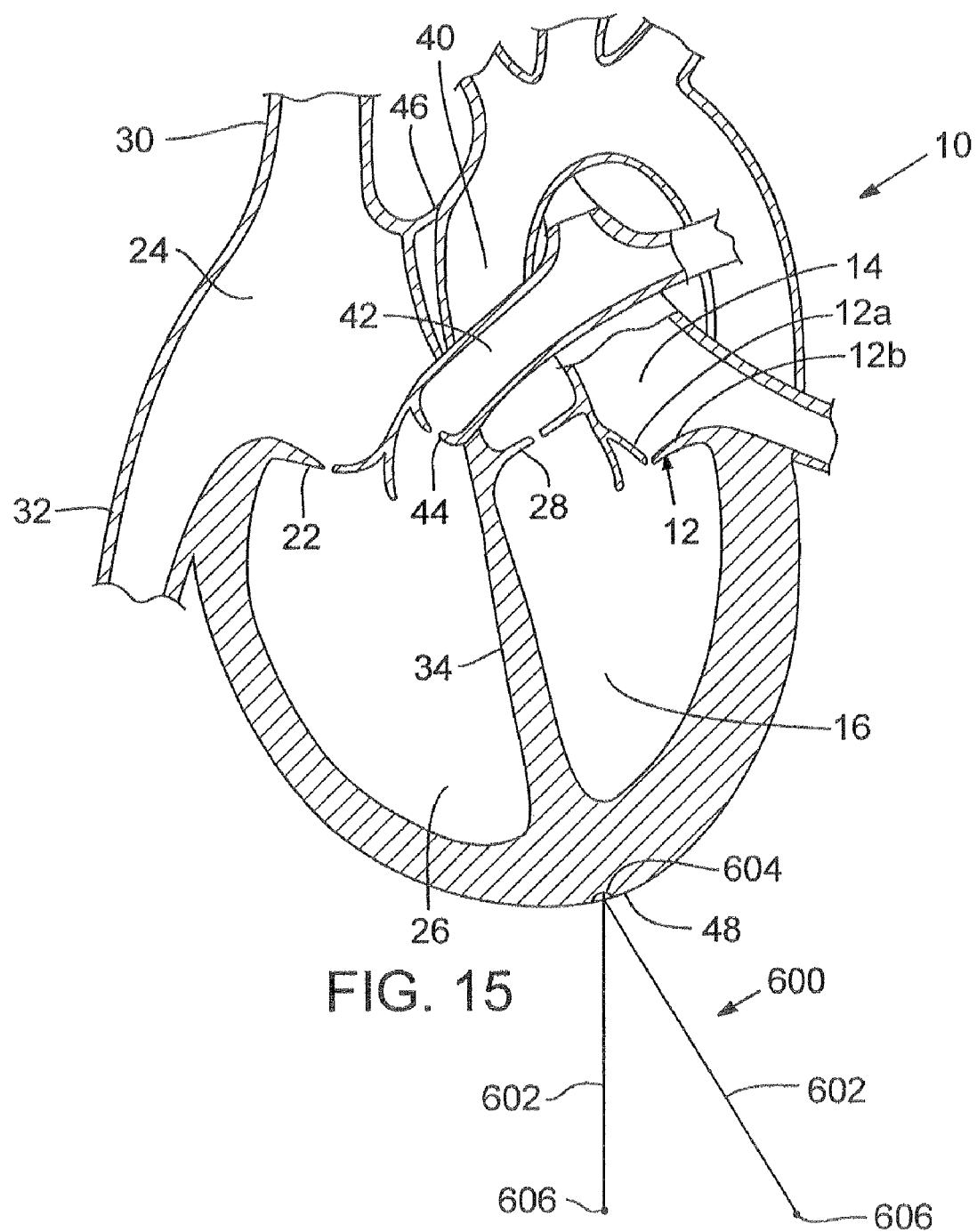
FIG. 15 is a cross-sectional view of a heart showing tension members secured to the outside of the heart at the apex for reshaping the heart, according to one embodiment.

With reference now to FIG. 15, another exemplary reshaping apparatus 600 configured to reshape the geometry of the heart is illustrated. In this embodiment, one or more tension members, or tethers, 602 (e.g., suture lines) are provided for pulling downward on the apex of the heart. In the illustrated embodiment, the upper ends of the tension members 602 are attached along the apex 48 of the heart (e.g., to the outside of the heart muscle) using a single anchor member 604 as shown or using a respective anchor member 604 for each tension member 602. The anchor member 604 can have a construction similar to the anchor member 500 described above. The lower ends 606 of the tension members can be fixed or tied off to a rigid structure within the body, such as a rib. Sufficient tension is applied to the tension members 602 to apply a longitudinal force to the apex that pulls the apex downwardly relative to the base of the heart. As can be appreciated, applying a pulling force to the outside of the heart is effective to reshape the geometry of the left and right ventricles.

Figure 16:
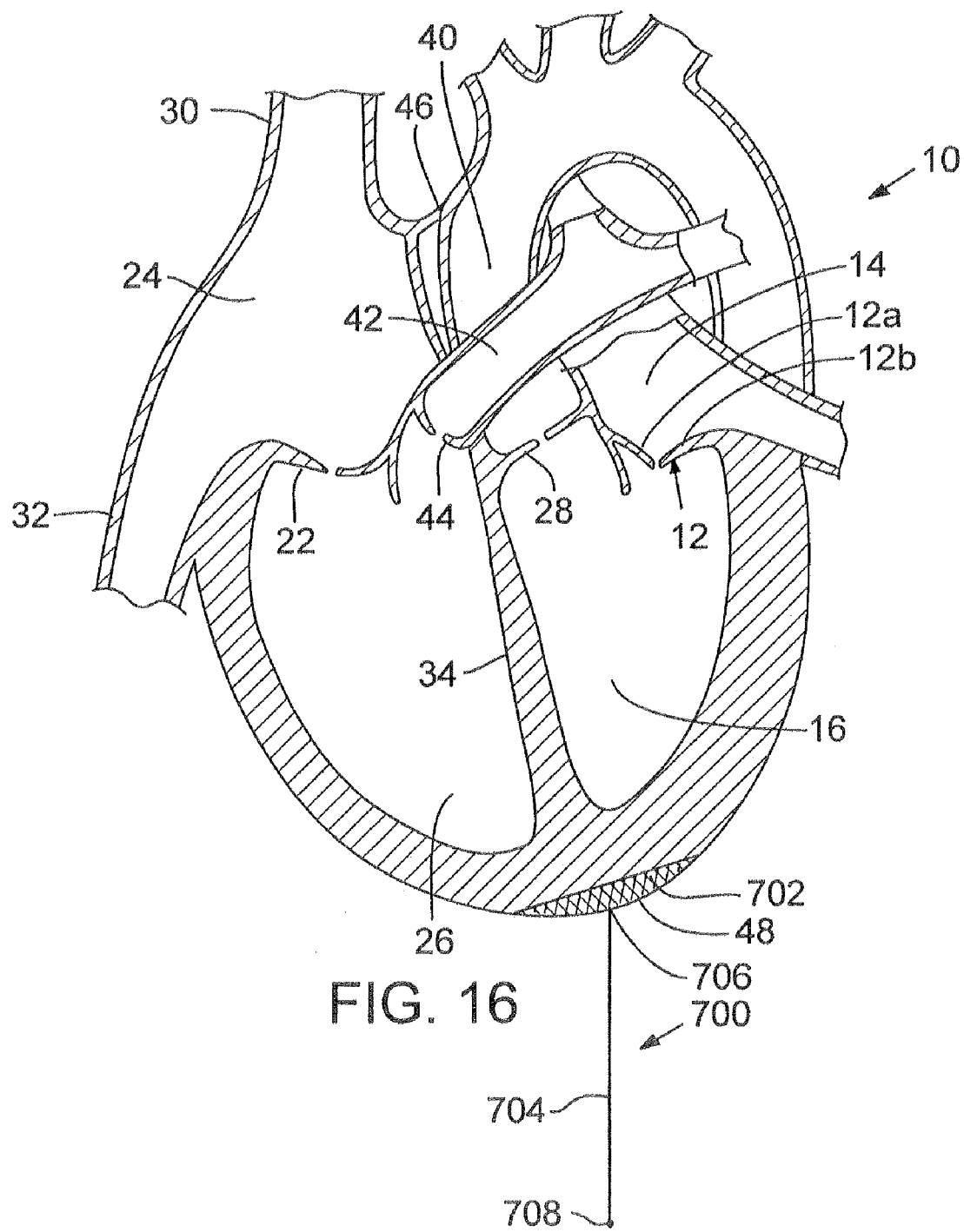
FIG. 16 is a cross-sectional view of a heart showing a tension member secured to the outside of the heart at the apex for reshaping the heart, according to another embodiment.

FIG. 16 shows a reshaping apparatus 700, according to another embodiment, that applies a force to the outside of the heart for reshaping the geometry of the heart. The apparatus 700 in the illustrated embodiment comprises a patch 702 that can be secured to the outer surface of the heart muscle along the apex 48. In one exemplary embodiment, a bioglue may be used to secure the patch 702 to the heart. A tension member 704 (e.g., a suture line) has an upper end 706 secured to the patch 702 and a lower end 708 that can be fixed or tied off to a rigid structure within the body, such as a rib. When securing the ends of the tension member, sufficient tension is applied to the tension member to pull the apex downwardly relative to the base of the heart to reshape both the left and right ventricles.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. I therefore claim as my invention all that comes within the scope and spirit of these claims.

I claim:

1. An apparatus for reshaping a dilated left ventricle of a human heart, comprising:
 an implantable body including an anchor member and an elongate pusher member comprising of a radially expandable stent having an unobstructed lumen extending therethrough, permanently fixed to the anchor member, the pusher member having a length sized to extend from a left ventricular outflow tract to an apex of the left ventricle, the anchor member having an expanded diameter sized for deployment in and permitting blood flow therethrough when implanted in the left ventricular outflow tract, the pusher member in a deployed state of the implantable body extending along a longitudinal axis from the anchor member to the apex of the left ventricle, the pusher member having a distal end portion adapted to apply a longitudinal force along the apex of the left ventricle to permanently elongate the left ventricle, thereby improving a pumping efficiency of the left ventricle;
 wherein the implantable body is configured to be delivered into the left ventricle by a delivery catheter and wherein the implantable body is configured for ejection from the delivery catheter for permanent implantation in the left ventricle.

2. The apparatus of claim 1, wherein the stent is self expanding.

3. The apparatus of claim 1, wherein the pusher member consists of a single elongate wire comprising an atraumatic tip shaped for engagement with an inner surface of the left ventricle.

4. The apparatus of claim 1, wherein the distal end portion of the pusher member is curved.

5. The apparatus of claim 4, wherein the pusher member comprises a lumen and a stylet slidably received in the lumen, the stylet being slidable into and out of the distal end portion to adjust the radius of curvature of the distal end portion so as to adjust the length of the pusher member.

6. The apparatus of claim 1, wherein the expanded diameter of the anchor member is sized to apply a lateral force that urges the anterior leaflet of a mitral valve toward the posterior leaflet, thereby improving leaflet coaption.

7. An apparatus for reshaping a ventricle of a heart, comprising:
 a radially expandable frame having an unobstructed lumen extending therethrough, substantially circular frame adapted to expand into contact with surrounding tissue to secure the frame at a fixed position in the heart, the frame being radially expandable about a longitudinal axis; and
 an elongated pusher member permanently fixed to and extending from the frame substantially in the direction of the longitudinal axis, the pusher member having a distal end portion adapted to engage and push against an inner surface portion of the ventricle to permanently distend the heart in a direction extending from the frame to the distal end portion of the pusher member.

8. The apparatus of claim 7, wherein the frame mounts a prosthetic valve.

9. The apparatus of claim 7, wherein the pusher member is J-shaped.

10. The apparatus of claim 7, wherein the pusher member is formed from a flat strip of material.

11. A device for reshaping a dilated left ventricle of a heart comprising:
 an insertion configuration and a deployed configuration;
 a longitudinal axis;
 an anchor member comprising a radially expandable stent having an unobstructed lumen extending therethrough, the anchor member deployable in juxtaposition with at least one of an aortic valve and a mitral valve, the anchor member permitting blood flow through the at least one of the aortic valve and the mitral valve in the deployed configuration; and
 a pusher member extending longitudinally from the anchor member, the pusher member comprising a proximal end coupled to the anchor member, and a distal end, the pusher member dimensioned such that the distal end applies a longitudinal force against an inferior inner surface portion of the left ventricle in the deployed configuration.

12. The device of claim 11, wherein the stent is self-expanding.

13. The device of claim 11, wherein the stent is balloon expandable.

14. The device of claim 11, wherein the anchor member comprises at least one of nitinol and stainless steel.

15. The device of claim 11, wherein the anchor member comprises at least one of attachment elements, barbs, staples, and flanges.

16. The device of claim 11, wherein the anchor member is dimensioned for deployment at least one of just beneath the aortic valve, within the aortic valve annulus, within the mitral valve annulus, and within the left atrium.

17. The device of claim 11, wherein the anchor member comprises a prosthetic valve assembly.

18. The device of claim 11, wherein a length of the pusher member is adjustable.

19. The device of claim 11, wherein the distal end of the pusher member comprises an arcuate, atraumatic flexible tip portion.

20. The device of claim 11, wherein the distal end of the pusher member is J-shaped.

21. The device of claim 11, wherein the pusher member comprises at least one of round wire; a flat ribbon; an elongate tube; a mesh; a solid, non-perforated material; a biocompatible material; stainless steel; and a polymer.

22. The device of claim 11, wherein, the device in the insertion configuration is insertable percutaneously through a peripheral artery.

23. The device of claim 11, wherein a diameter of the anchor member in the insertion configuration is smaller than a diameter of the anchor member in the deployed configuration.

* * * * *